(12) United States Patent
Allwein et al.

(10) Patent No.: US 10,259,794 B2
(45) Date of Patent: Apr. 16, 2019

(54) METHODS FOR PREPARING FUSED BICYCLIC 2, 4-DIAMINOPYRIMIDINE DERIVATIVES

(71) Applicant: CEPHALON, INC., Frazer, PA (US)

(72) Inventors: Shawn P. Allwein, Downingtown, PA (US); Roger P. Bakale, San Diego, CA (US); Dale R. Mowrey, Glenmoore, PA (US); Daniel E. Petrillo, Doylestown, PA (US); Sander Kluwer, Amsterdam (NL)

(73) Assignee: CEPHALON, INC., Frazer, PA (US)

( * ) Notice: Subject to any disclaimer, the term of this patent is extended or adjusted under 35 U.S.C. 154(b) by 0 days.

(21) Appl. No.: 15/537,954

(22) PCT Filed: Dec. 23, 2015

(86) PCT No.: PCT/US2015/000301
§ 371 (c)(1),
(2) Date: Jun. 20, 2017

(87) PCT Pub. No.: WO2016/105529
PCT Pub. Date: Jun. 30, 2016

(65) Prior Publication Data
US 2017/0369451 A1 Dec. 28, 2017

Related U.S. Application Data

(60) Provisional application No. 62/095,861, filed on Dec. 23, 2014.

(51) Int. Cl.
| C07D 241/04 | (2006.01) |
| C07D 295/135 | (2006.01) |
| C07D 403/12 | (2006.01) |
| A61K 31/495 | (2006.01) |

(52) U.S. Cl.
CPC .......... *C07D 241/04* (2013.01); *A61K 31/495* (2013.01); *C07D 295/135* (2013.01); *C07D 403/12* (2013.01)

(58) Field of Classification Search
CPC ............................ A61K 31/495; C07D 241/04
See application file for complete search history.

(56) References Cited

FOREIGN PATENT DOCUMENTS

| WO | 2013/134353 | | 9/2013 | | |
| WO | WO 2013/134353 | * | 9/2013 | ........... | C07D 403/04 |

* cited by examiner

*Primary Examiner* — Erich A Leeser
(74) *Attorney, Agent, or Firm* — Sterne, Kessler, Goldstein & Fox P.L.L.C.

(57) ABSTRACT

The present disclosure is directed to improved methods useful for the preparation of, for example, 2-[[5-chloro-2-[[(6S)-6-[4-(2-hydroxyethyl)piperazin-1-yl]-1-methoxy-6,7,8,9-tetrahydro-5Hbenzo[7]annulen-2-yl]amino]pyrimidin-4-yl]amino]-N-methyl-benzamide (CEP-37440).

36 Claims, No Drawings

METHODS FOR PREPARING FUSED BICYCLIC 2, 4-DIAMINOPYRIMIDINE DERIVATIVES

CROSS-REFERENCE TO RELATED APPLICATIONS

This application is a National Stage Application filed under 35 U.S.C. 371 of International Application No. PCT/US2015/000301 filed Dec. 23, 2015, which claims the benefit of priority of U.S. Provisional Application No. 62/095,861, filed Dec. 23, 2014, the entirety of which is hereby incorporated by reference herein.

BACKGROUND

2-[[5-chloro-2-[[(6S)-6-[4-(2-hydroxyethyl)piperazin-1-yl]-1-methoxy-6,7,8,9-tetrahydro-5Hbenzo[7]annulen-2-yl]amino]pyrimidin-4-yl]amino]-N-methyl-benzamide (CEP-37440) is an orally available dual kinase inhibitor of the receptor tyrosine kinase anaplastic lymphoma kinase (ALK) and focal adhesion kinase (FAK) with antineoplastic activity. See, e.g., WO 2013/134353.

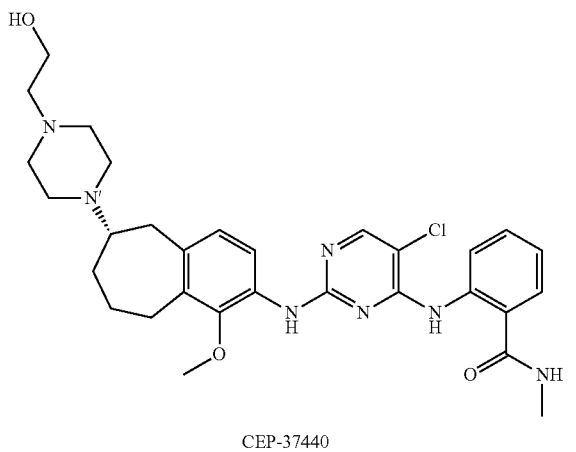

CEP-37440

In view of the surprising and unexpected properties observed with CEP-37440, improved methods for its preparation in high enantiomeric purity are needed.

SUMMARY

The disclosure is directed to methods of resolving mixtures of compounds IA

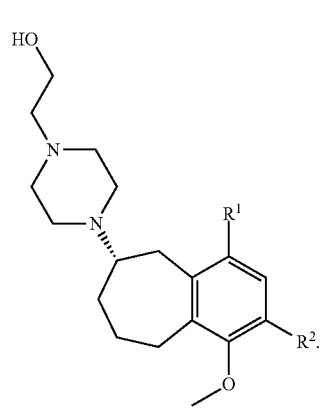

IA

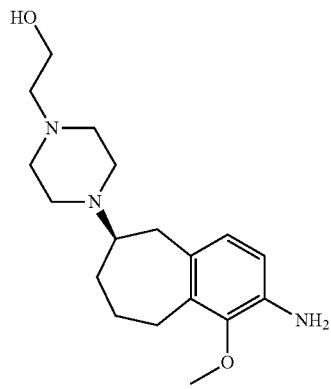

IB in the presence of L-tartaric acid; in a solvent system comprising an alcohol and water; to produce the L-tartaric acid salt of the compound IA.

The disclosure is also directed to methods comprising contacting a compound of formula IV, or a salt form thereof

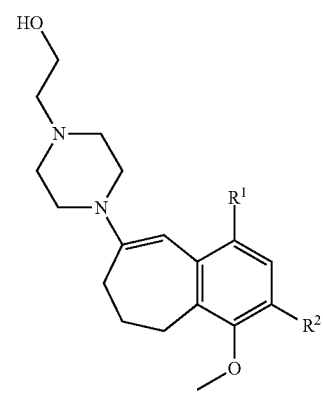

IV wherein $R^1$ is H, Cl, Br, or I; and $R^2$ is $NO_2$ or $NH_2$; with a first hydrogenation catalyst, a ligand, and optionally an additive, in the presence of hydrogen to form a compound of formula V, or a salt form thereof (V)

Methods comprising contacting a compound of formula VI, or a salt form

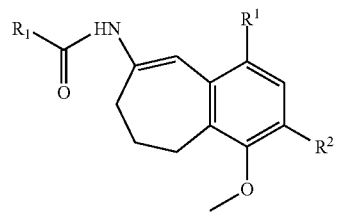

VI wherein $R_1$ is $C_{1-6}$alkyl; with hydrogen, a chiral hydrogenation catalyst, and an acid; in the presence of an organic solvent; for a time and at a temperature sufficient to produce a compound of formula VII, or a salt form thereof

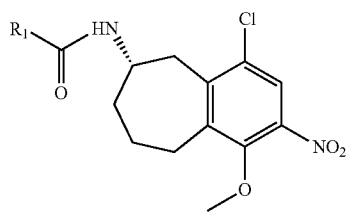

VII are also described.

DETAILED DESCRIPTION OF ILLUSTRATIVE EMBODIMENTS

All ranges disclosed herein are inclusive of the recited endpoint and independently combinable (for example, the range of "from 2 to 10" is inclusive of the endpoints, 2 and 10, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 2 to about 10" also discloses the range "from 2 to 10." The term "about" may refer to plus or minus 10% of the indicated number. For example, "about 10" may indicate a range of 9 to 11, and "about 1" may mean from 0.9 to 1.1. Other meanings of "about" may be apparent from the context, such as rounding off, so, for example "about 1" may also mean from 0.5 to 1.4.

The present disclosure is directed to improved processes for the preparation of 2-[[5-chloro-2-[[(6S)-6-[4-(2-hydroxyethyl)piperazin-1-yl]-1-methoxy-6,7,8,9-tetrahydro-5Hbenzo[7]annulen-2-yl]amino]pyrimidin-4-yl]amino]-N-methyl-benzamide (CEP-37440). The present disclosure is also directed to improved processes for preparing asymmetric intermediate compounds that can be used to prepare CEP-37440, or any other pharmaceutical or commercial compound.

One embodiment of the present disclosure is directed to methods of resolving a mixture of compounds IA and IB:

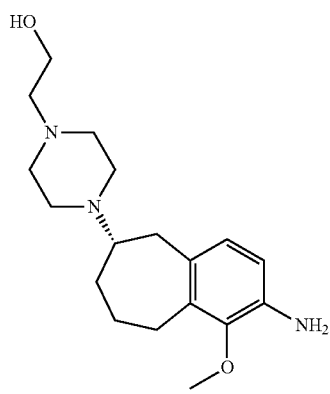

IA

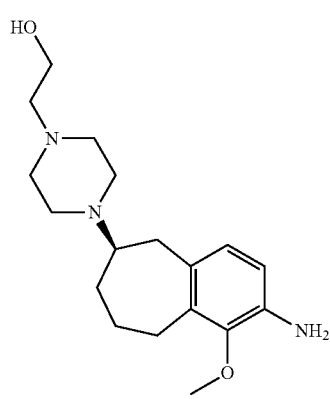

IB

Those skilled in the art will readily appreciate that compounds IA and IB are enantiomers of one another. The mixture of compounds IA and IB can include each individual compound in any proportion. For example, the mixture can contain compounds IA and IB in about a 1:1 ratio. Ratios of between about 1:10 and about 10:1 are also envisioned as being suitable for use in the described resolving methods.

As used herein, "resolving" refers to the process of increasing the proportion of one enantiomer in a mixture, relative to the proportion of that enantiomer in the starting mixture, i.e., increasing the enantiomeric excess (ee) of one enantiomer. In preferred embodiments, the proportional increase, i.e., increase in ee, will be at least about 10%, with at least 20%, 30%, and at least 40% being particularly preferred. "Resolving" also refers to the process of increasing the proportion of one diastereomer in a mixture, relative to the proportion of that diastereomer in a starting mixture, i.e., increasing the diastereometric excess (de) of one diastereomer. In preferred embodiments, the proportional increase, i.e., increase in de, will be at least about 10%, with at least 20%, 30%, and at least 40% being particularly preferred.

In one embodiment, the mixture of compounds IA and IB are resolved in the presence of L-tartaric acid or D-tartaric acid in a solvent system comprising an alcohol and water. It has been discovered that tartaric acid is a far superior resolving agent, as compared to other chiral salts that have been used in the art for resolving mixtures of compounds.

The solvent system can comprise between about 5% and about 20% (v/v) of water, with about 10% being preferred.

In exemplary embodiments, the alcohol is methanol, ethanol, or a propanol, or a mixture thereof, with methanol being particularly preferred.

The resolving step can be carried out at temperatures of between about 15° C. to about 40° C. Preferably, the resolving step is carried out at a temperature of about 15, 20, 25, 30, 35, or about 40° C.

The concentration of the mixture of compounds IA and IB in the solvent system is about 0.02 g/mL to about 1 g/mL. For example, the concentration of the mixture of compounds IA and IB in the solvent system can be about 0.02, 0.03, 0.04, 0.05, 0.06, 0.07, 0.08, 0.09, 0.1, 0.2, 0.3, 0.4, 0.5, 0.6, 0.7, 0.8, 0.9, or about 1 g/mL.

In those embodiments employing L-tartaric acid, the L-tartaric acid salt of the compound IA will preferentially crystallize from the resolving mixture over the L-tartaric acid salt of the compound IB. The L-tartaric acid salt of the compound IA can be separated from the resolving mixture using methods known in the art, for example, filtration or decantation. The diastereometric excess ("de") of the L-tartaric acid salt of the compound IA, which can be measured using methods known in the art, for example, chiral high performance liquid chromatography (HPLC), isolated after the resolving step, is at least about 20%. More preferably, the de is at least about 25, 30, 35, 40, 45, 50, 55, 60, 65, 70, 75, 80, 85, 90, 95, or at least about 99%, after the resolving step.

In other embodiments of the disclosure, the de of the L-tartaric acid salt of the compound IA can be increased by performing additional iterations of the resolving methods. For example, the resolving methods described herein can be performed two, three, four, five, or more times.

In yet other embodiments, the de of the L-tartaric acid salt of the compound IA can be increased by recrystallizing the L-tartaric acid salt of the compound IA obtained after resolution, using methods known in the art.

Those skilled in the art understand that the L-tartaric acid acid of the compound IA can be readily converted to the corresponding free base compound IA. When using the methods disclosed herein, the compound IA will have an ee that is at least about 10%, at least 20%, at least 30%, or at least 40% greater that the ee of a starting mixture of compounds IA and IB.

In those embodiments employing D-tartaric acid, the D-tartaric acid salt of the compound IB will preferentially crystallize from the resolving mixture over the D-tartaric acid salt of the compound IA. The D-tartaric acid salt of the compound IB can be separated from the resolving mixture using methods known in the art, for example, filtration or decantation. The enantiomeric excess ("de") of the D-tartaric acid salt of the compound IB, which can be measured using methods known in the art, for example, chiral HPLC, isolated after the resolving step, is at least about 20%. More preferably, the de is at least about 25, 30, 35, 40, 45, 50, 55, 60, 65, 70, 75, 80, 85, 90, 95, or at least about 99%, after the resolving step.

In other embodiments of the disclosure, the de of the D-tartaric acid salt of the compound IB can be increased by performing additional iterations of the resolving step. For example, the resolving step can be performed two, three, four, five, or more times.

In yet other embodiments, the de of the D-tartaric acid salt of the compound IB can be increased by recrystallizing the D-tartaric acid salt of the compound IB obtained after resolution using methods known in the art.

Those skilled in the art understand that the D-tartaric acid acid of the compound IB can be readily converted to the corresponding free base compound IB. When using the methods disclosed herein, the compound IB will have an ee that is at least about 10%, at least 20%, at least 30%, or at least 40% greater that the ee of a starting mixture of compounds IA and IB.

The disclosure is also directed to methods of asymmetrically hydrogenating a compound of formula IV, or a salt form thereof:

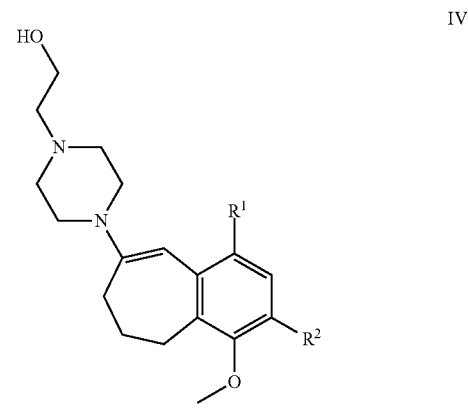

wherein $R^1$ is H, Cl, Br, or I; and $R^2$ is $NO_2$ or $NH_2$; to form a compound of formula V, of a salt form thereof:

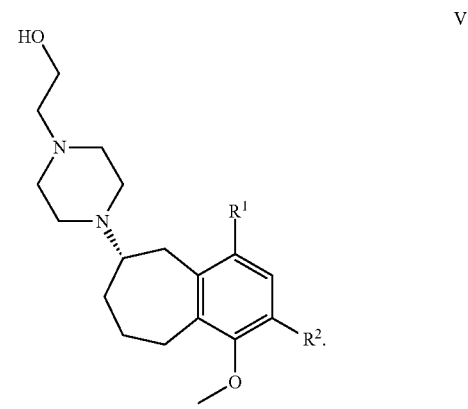

In some embodiments, $R^1$ is a halogen, for example, Cl, Br, or I, with Cl being particularly preferred. In exemplary embodiments, $R^1$ is Cl and $R^2$ is $NO^2$. In other embodiments, $R^1$ is Cl and $R_2$ is $NH_2$. In still other embodiments, $R^1$ is H. In some embodiments, $R^2$ is $NO_2$. In other embodiments, $R^2$ is $NH_2$.

In preferred embodiments of the disclosure, the asymmetric hydrogenating methods comprise contacting a compound of formula IV, or a salt form thereof, with a first hydrogenation catalyst, a ligand, and optionally an additive, in the presence of hydrogen to form a compound of formula V, or a salt form thereof.

In the methods of the disclosure, it is theorized that the first hydrogenation catalyst and the ligand forms a catalyst-ligand complex in situ. Such catalyst-ligand complexes are also within the scope of the disclosure. Supramolecular catalyst systems are also within the scope of the disclosure.

In some embodiments of the invention, the first hydrogenation catalyst is an iridium catalyst, a rhodium catalyst, or a ruthenium catalyst, with iridium catalysts being particularly preferred. An exemplary iridium catalyst is bis((μ-chloro)bis(cyclooctene)iridium.

Ligands for use in the disclosure include phosphoramidite ligands, phosphine ligands, and bidentate ligands. Exemplary ligands include WALPHOS [(R)-1-{(R$_P$)-2-[2-[bis(4-methoxy-3,5-dimethylphenyl)phosphino]phenyl]ferrocenyl}ethylbis[3,5-bis(trifluoromethyl)phenyl]phosphine], DUANPHOS [(1R,1'R,2S,2'S)-2,2'-di-tert-butyl-2,3,2',3'-tetrahydro-1H,1'H-(1,1')biisophosphindolyl], DUPHOS [(+)-1,2-Bis[(2R,5R)-2,5-diisopropylphospholano]benzene], INDOLPHOS (commercially available from InCatT B.V., The Netherlands), METAMORPHOS (see, e.g., WO 2009/065856), SEGPHOS [(R)-(+)-5,5'-Bis(diphenylphosphino)-4,4'-bi-1,3-benzodioxole], (R)-T-BINAP [(R)-(+)-2,2'-Bis(di-p-tolylphosphino)-1,1'-binaphthyl], MANDYPHOS [(R$_P$,R'$_P$)-1,1'-bis{bis[3,5-bis(trifluoromethyl)phenyl]phosphino}-2,2'-bis[(S)-α-(dimethylamino)benzyl]ferrocene], CHIRAPHOS [(2S,3S)-(−)-bis(diphenylphosphino)butane], with METAMORPHOS being particularly preferred. Ligands are commercially available for purchase or can be readily prepared using methods described in the art.

The methods for asymmetric hydrogenating a compound of formula IV to produce a compound of formula V can be achieved in the presence of an additive. One class of additives that can be used in the methods of the disclosure are borates, for example, sodium tetrakis[3,5-bis(trifluoromethyl)phenyl]borate. Another class of additives is amine bases, for example Et$_3$N, diisopropylamine, diisopropylethylamine, and the like, with Et$_3$N being particularly preferred. Yet another class of additives is carbonates, for example, K$_2$CO$_3$, Na$_2$CO$_3$, CaCO$_3$, and the like, with K$_2$CO$_3$ being particularly preferred.

The methods of the disclosure for asymmetric hydrogenating a compound of formula IV to produce a compound of formula V can alternatively be achieved without an additive being present.

In preferred embodiments, the pressure of the hydrogen used in the methods for asymmetric hydrogenating a compound of formula IV to produce a compound of formula V is at least 1 atm. In other embodiments, the pressure of the hydrogen used in the methods is greater than 1 atm to about 60 atm, preferably about 40 atm to about 60 atm or about 20 atm. to about 50 atm. For example, the pressure of the hydrogen used in the methods is about 10, 15, 20, 25, 30, 35, 40, 45, 50, 55, or 60 atm.

The methods for asymmetric hydrogenating a compound of formula IV to produce a compound of formula V can be carried out at about ambient temperature or higher, for example, about 20° C. to about 70° C., preferably about 20° C. to about 50° C. For example, the methods of the disclosure can be carried out at about 20, 25, 30, 35, 40, 45, 50, 55, 60, 65, or about 70° C.

According to the disclosure, the asymmetric hydrogenation of a compound of formula IV to produce a compound of formula V can be carried out in an organic solvent or mixture of organic solvents. Preferred solvents include, for example, dichloromethane (DCM), tetrahydrofuran (THF), an alcoholic solvent (methanol, ethanol, isopropanol, trifluoroethanol, and the like), and combinations thereof. One preferred solvent is dichloromethane. Another preferred solvent is a mixture of trifluoroethanol and dichloromethane.

According to the disclosure, the asymmetric hydrogenation of a compound of formula IV to produce a compound of formula V can produce the compound of formula V having an ee of at least about 20%. More preferably, the ee is at least about 25, 30, 35, 40, 45, 50, 55, 60, 65, 70, 75, 80, 85, 90, 95, or at least about 99%.

The disclosure is also directed to methods of producing the compound IA from a compound of formula V. According to these methods, a compound of formula V is contacted with hydrogen and a second hydrogenation catalyst for a time sufficient to produce the compound IA. Hydrogenation catalysts useful in converting a compound of formula V to the compound IA are known in the art and include, for example, palladium, platinum, and rhodium catalysts. Particularly preferred second hydrogenation catalysts include Pd/C and Pd(OH)$_2$/C.

In the methods of the disclosure converting a compound of formula V to the compound IA, the pressure of the hydrogen can be about 1 atm or higher. In some embodiments, the pressure of the hydrogen can be about 1 atm to about 8 atm. For example, the pressure of the hydrogen can be about 1, 1.5, 2, 2.5, 3, 3.5, 4, 4.5, 5, 5.5, 6, 6.5, 7, 7.5, or about 8 atm.

In some embodiments of the disclosure, the compound IA can be converted to a salt form in order to, for example, facilitate purification. A particularly preferred salt form is the tartrate salt of the compound IA.

Within the scope of the disclosure, suitable salt forms of any of the described compounds include pharmaceutically acceptable salts such as, for example, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate.

The disclosure is also directed to methods of converting a compound of formula II, or a salt form thereof

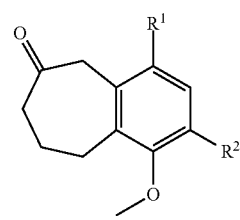

II to a compound of formula IV, or a salt form thereof. These methods comprise contacting a compound of formula II, or a salt for thereof, with a compound of formula III, or a salt form thereof

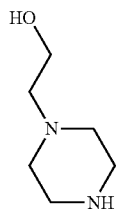

III

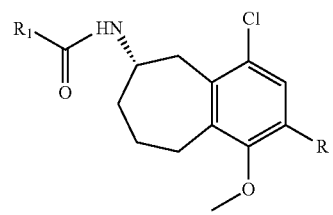

VII for a time and under conditions sufficient to produce the compound of formula IV, or a salt form thereof.

The conversion of a compound of formula II to a compound of formula IV can be conducted in an organic solvent, for example, dichloromethane, hexanes, heptane, tetrahydrofuran, or a mixture thereof, at ambient temperature or higher.

The disclosure is also directed to methods of producing a compound of formula II, wherein $R_2$ is $NO_2$, comprising contacting a compound of formula IIA, or a salt form thereof

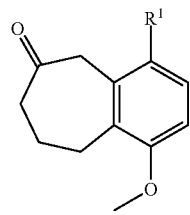

IIA with a nitrate in the presence of an acid, to form a compound of formula II. In some embodiments of the disclosure, the nitrate is potassium nitrate or sodium nitrate. In other embodiments of the disclosure, the acid is trifluoroacetic acid, methanesulfonic acid, or sulfuric acid. Trifluoroacetic acid is a particularly preferred acid and it has been observed that compounds of formula II have little to no solubility in trifluoroacetic acid, which facilitates isolation of the product from the reaction mixture. In other embodiments of the invention, these methods can include an optional step of reducing the $NO_2$ moiety to form a compound of formula II wherein $R^2$ is $NH_2$. Methods of reducing an $NO_2$ moiety to produce an $NH_2$ moiety are known in the art and include catalytic hydrogenation, for example.

The disclosure is also directed to methods of asymmetrically hydrogenating a compound of formula VI, or a salt form thereof

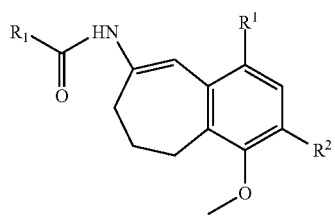

VI wherein $R^3$ is $C_{1-6}$alkyl. Preferably, the $C_{1-6}$alkyl is methyl, ethyl, propyl, isopropyl, butyl, or t-butyl, with methyl being particularly preferred.

According to these methods, a compound of formula VI, or salt form thereof, is converted to a compound of formula VII, wherein R is $-NO_2$ or $-NH_2$, or a salt form thereof These methods comprise contacting a compound of formula VI, or a salt form thereof, with hydrogen, a chiral hydrogenation catalyst, and an acid, in the presence of an organic solvent, for a time and at a temperature sufficient to produce the compound of formula VII, or a salt form thereof.

In some embodiments, the compound of formula VII is a compound of formula VII-A or VII-B:

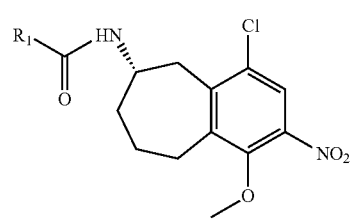

VII-A

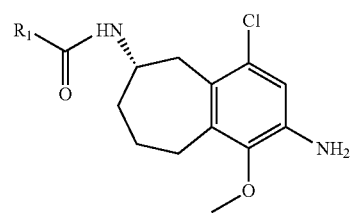

VII-B

In preferred embodiments, the chiral hydrogenation catalyst is $Ru(R-C_3-TunePhos)(acac)_2$, $Ru(R-C_3-TunePhos)(OAc)_2$, $Rh(COD)(SCRP-DuanPhos)BF_4$, or $Ru(S-C_5-TunePhos)(acac)_2$. Mixtures of chiral hydrogenation catalysts are also envisioned.

In some embodiments, the organic solvent is an alcohol, toluene, or a combination thereof. In preferred embodiments, the alcohol is methanol or ethanol, or a combination thereof.

In other embodiments, the acid is a mineral acid, for example, hydrochloric acid, sulfuric acid, or phosphoric acid. A preferred mineral acid is phophoric acid.

The pressure of the hydrogen used in these methods is preferably above atmospheric pressure, for example, between about 10 atm and about 100 atm, for example, between about 15 atm and about 70 atm. Preferred hydrogen pressures for use in producing a compound of formula VII include about 10, 15, 20, 25, 30, 35, 40, 45, 50, 55, 60, 65, 70, 75, 80, 85, 90, 95, or about 100 atm.

The conversion of a compound of formula VI, or salt form thereof, to a compound of formula VII, or a salt form thereof, can be carried out above ambient temperature, for example, between about 25° C. to about 85° C. Preferred reaction temperatures include about 25, 30, 35, 40, 45, 50, 55, 60, 65, 70, 75, 80, or about 85° C.

In preferred embodiments of these methods, a compound of formula VII, or a salt form thereof, is produced having an ee of at least about 20%. More preferably, the ee is at least about 25, 30, 35, 40, 45, 50, 55, 60, 65, 70, 75, 80, 85, 90, 95, or at least about 99%.

In other embodiments of the disclosure, a compound of formula VII, or salt form thereof, is contacted with (2,6-dioxo-morpholin-4-yl)-acetic acid, or a derivative thereof, for a time and under conditions sufficient to produce a compound of formula VIII, wherein R is —NO$_2$ or —NH$_2$, or a salt form thereof

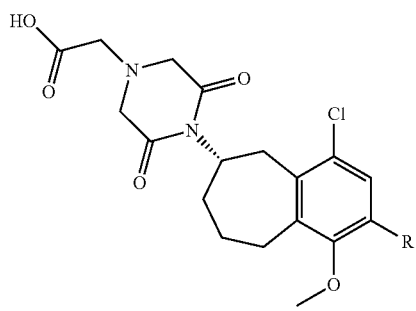

VIII

In some embodiments, the compound of formula VIII is compound VIII-A or compound VIII-B:

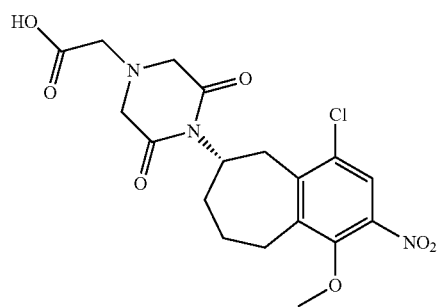

VIII-A

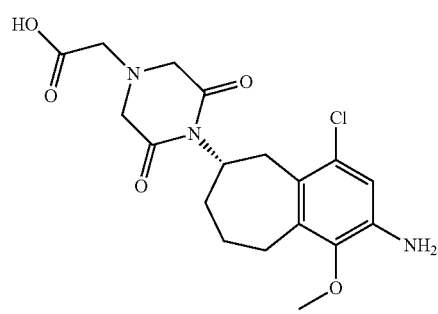

VIII-B

In yet other embodiments of the disclosure, the compound of formula VIII, or a salt form thereof, is subjected to reducing conditions known in the art to form the compound IA, or a salt form thereof.

Other embodiments of the disclosure comprise contacting a compound of formula IX

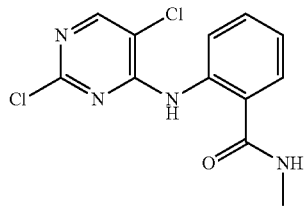

IX with the compound IA, or a salt form thereof, produced according to any of the methods described herein, to produce CEP-37440, or a salt form thereof

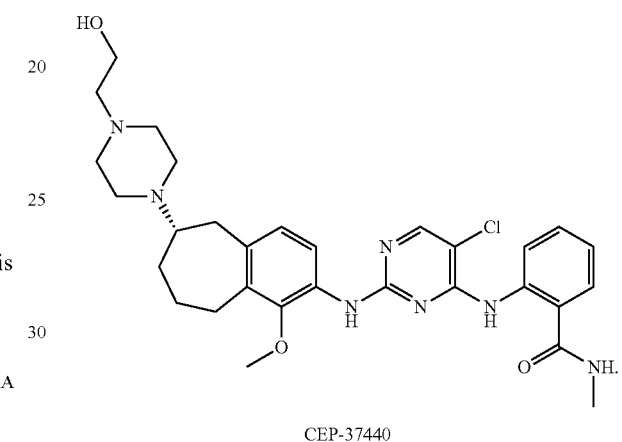

CEP-37440

Particularly preferred methods for producing the tartrate salt of the "A-Ring" used in the preparation of CEP-37440 according to the disclosure are set forth in Scheme 1.

Scheme 1

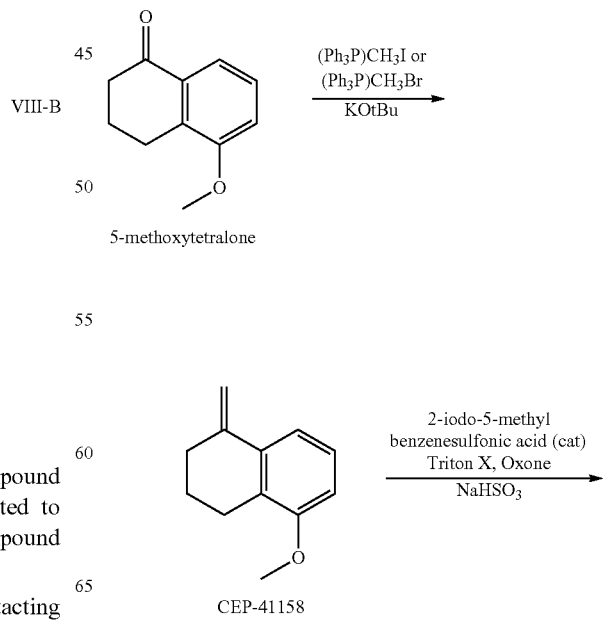

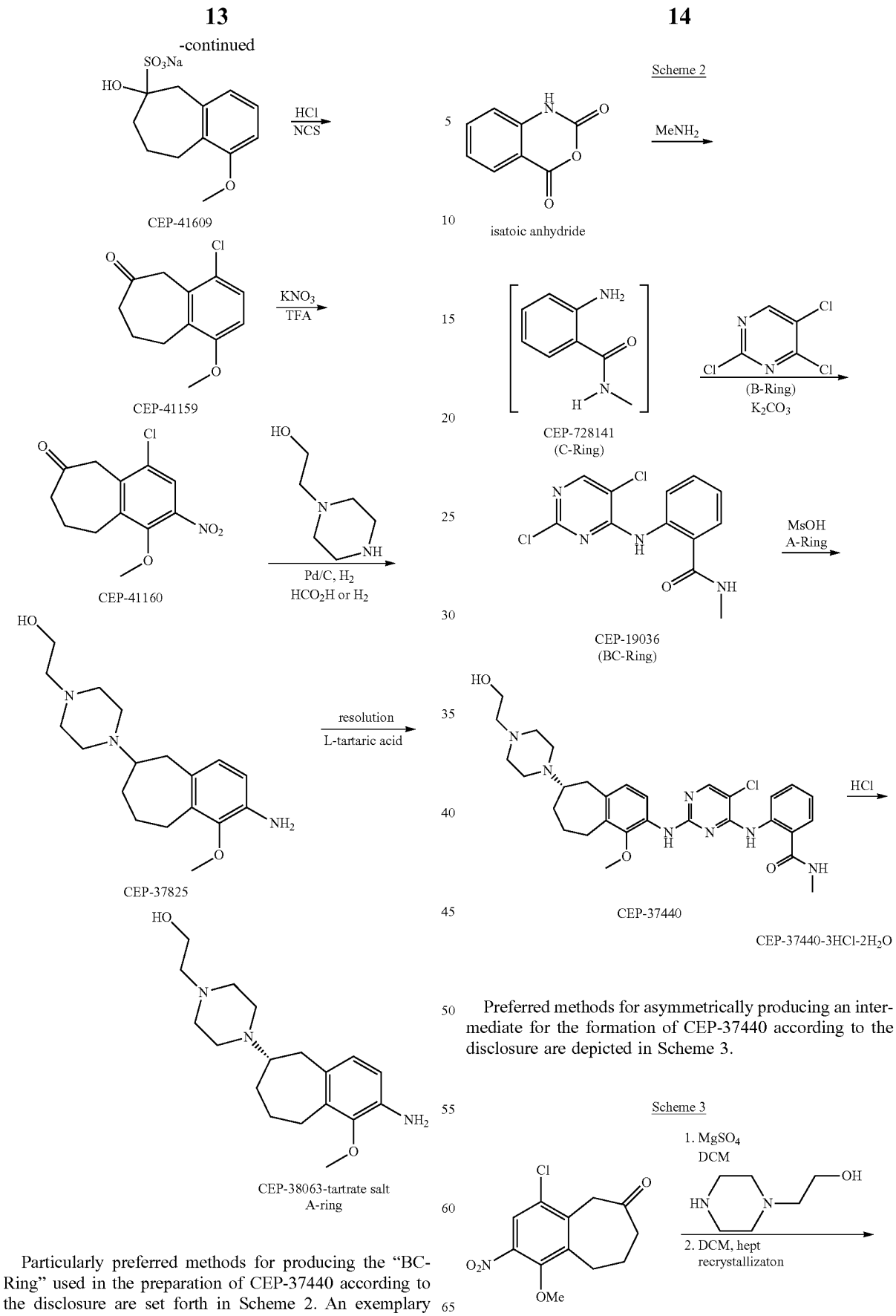

Particularly preferred methods for producing the "BC-Ring" used in the preparation of CEP-37440 according to the disclosure are set forth in Scheme 2. An exemplary method for coupling A-Ring with BC-Ring to form CEP-37440 is also depicted in Scheme 2.

Preferred methods for asymmetrically producing an intermediate for the formation of CEP-37440 according to the disclosure are depicted in Scheme 3.

15

-continued

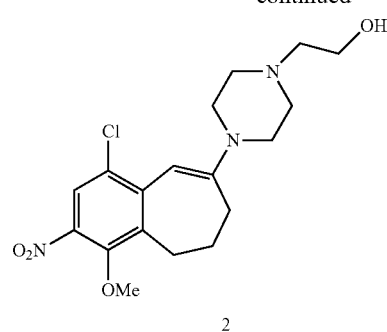

2

[Ir(COE)Cl]$_2$
METAMORPhos
CF$_3$CH$_2$OH/DCM
H$_2$ (50 bar), NaBArF
→

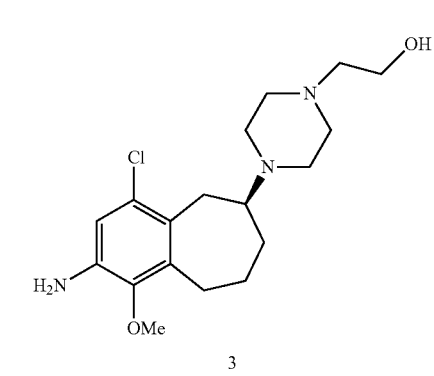

3

Pd/C
H$_2$, 1 atm
→

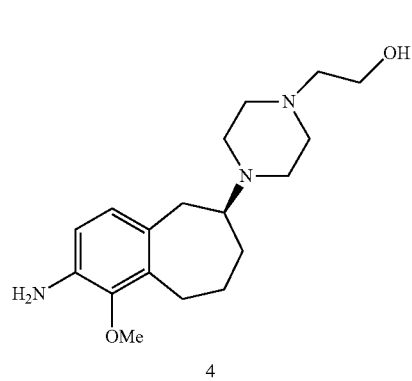

4 salt formation
→

CEP-38063 tartrate salt

Preferred methods for asymmetrically producing an intermediate for the formation of CEP-37440 according to the disclosure are depicted in Scheme 4.

16

Scheme 4

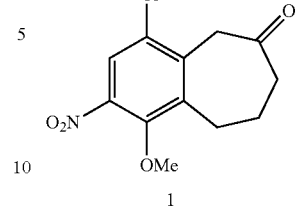

1 enamide formation
→

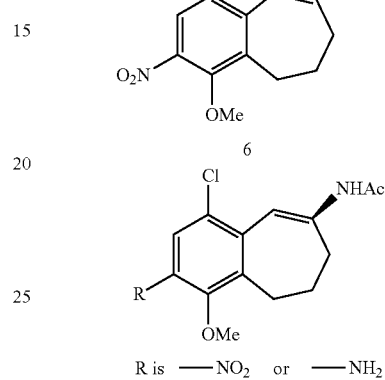

6 asymmetric hydrogenation
→

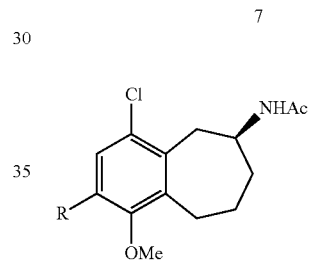

7

R is —NO$_2$ or —NH$_2$ hydrolysis
→

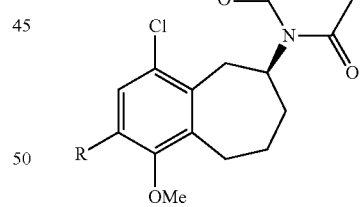

8

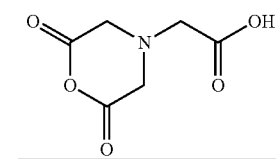

→

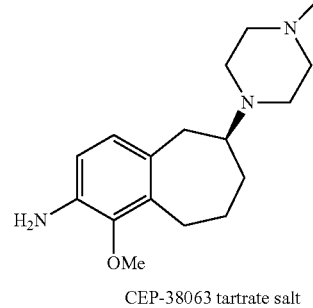

9 reduction
→

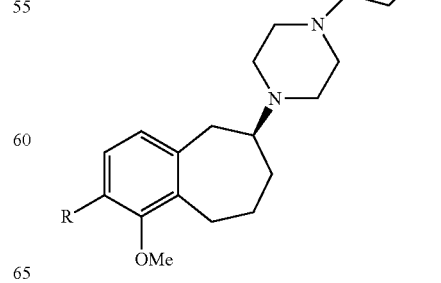

10

1. hydrogenation
2. salt formation
→

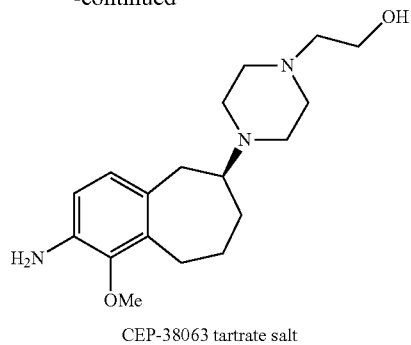

CEP-38063 tartrate salt

The following examples are provided to illustrate the compositions, processes, and properties of the present disclosure. The examples are merely illustrative and are not intended to limit the disclosure to the materials, conditions, or process parameters set forth therein.

All publications, patent applications, patents and other references mentioned herein are incorporated by reference in their entirety.

EXAMPLES

Chiral HPLC method:
CHIRALCEL AD column
eluent: heptane/isopropanol (90:10)
flow: 1.2 mL/min
detection: 220 nm and 254 nm.

Example 1

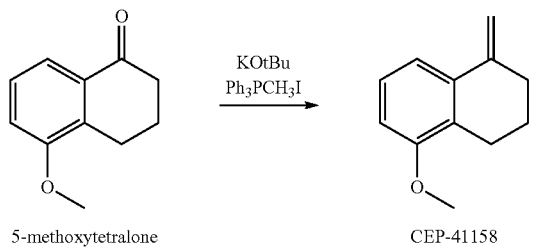

To a 12 L 4-neck round bottom flask was added methoxytetralone (500 g, 2830 mmol, 1 eq) and Ph₃PCH₃I (1320 g, 3264 mmol, 1.15 eq) as solids via a powder funnel. THF (5 L) was added and the mixture was stirred with overhead stirring at 19° C. tBuOK (525 g, 4683, 1.65 eq) was added portion-wise over 2 hours to maintain a maximum reaction temperature of 47° C. A THF solution of tBuOK can also be used with similar results. The funnel was washed with additional THF as needed. The resulting slurry was stirred for an additional hour at 30° C. HPLC analysis showed <0.5% starting material.

The reaction was transferred to a single neck flask and concentrated by roto-evaporator and solvent switched to heptanes (approximately 2.5 L, removing as much THF as possible). The slurry was filtered, washing with an additional 0.5 L heptanes. The combined filtrant and wash (approximately 3 L) was washed 2 times with water (2×250 mL). The water layers were back extracted 1 time with 0.5 L heptanes which was combined with the other organic layers (total volume was approximately 3.5 L).

To remove the residual amounts of Ph₃PO, the solution can be dried and cooled (overnight in the cold room) to precipitate out the triphenylphosphine oxide. Filtration results in a clean product stream that can be concentrated to an oil. Alternatively, the initial heptane product stream may be passed through a plug of SiO₂ followed by concentration to an oil.

Example 2

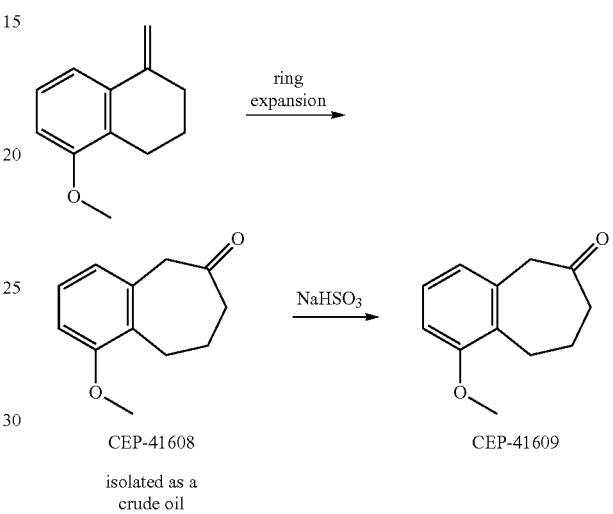

CEP-41608
isolated as a
crude oil

CEP-41609

CEP-41158 (Limiting Reagent, see Example 1) was charged to a reaction vessel followed by methyl tertiary butyl ether (MTBE) (6.3 volumes), isopropanol (3.3 volumes), Triton X (0.1 volumes), water (6.3 volumes), and 2-iodo-5-methylbenzenesulfonic acid (0.125 eq). While holding the batch at 20-25° C., oxone (0.65 eq) was added portion-wise over approximately 1.5 h and then continued to stir at room temperature. HPLC was used to monitor reaction conversion. A typical reaction time was 4 h but the reaction can be stirred overnight, as well.

The reaction was quenched by the slow addition of sodium sulfite (0.5 eq) over 10 minutes. Peroxide test strips were used to confirm no peroxides remained. NaOH (5N) was then added at <30° C. to obtain a pH of 8 (typically this was approximately 2 volumes of 5N NaOH). Celite was added and the solution was filtered. The aqueous layer was removed and the organics were washed with brine before being concentrated to an oil.

Bisulfite adduct formation: The above oil was taken up in isopropanol (7 volumes) before adding water (4 volumes). To this solution was slowly added a freshly prepared aqueous sodium bisulfate solution (6.4 M, 2 eq) at ambient temperature. The resulting slurry was stirred overnight then filtered. The solids were washed with isopropanol and then dried at 40° C. in a vacuum oven with a nitrogen bleed.

Example 3

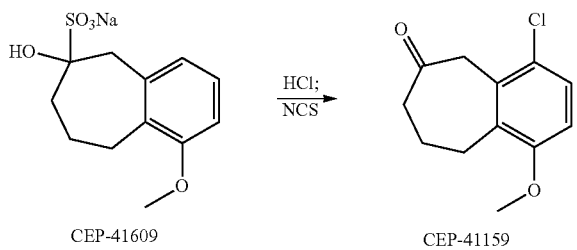

CEP-41609 → (HCl; NCS) → CEP-41159

Unless otherwise noted all volumes and equivalents are based on the wt % corrected charge of CEP-41609. To a nitrogen purged 2.0 L jacketed reactor equipped with an anchor overhead stirrer, and a thermocouple probe was charged 117.8 g of CEP-41609 (84.9 wt %, 100.0 g, 0.3398 mol). 500 mL of acetonitrile (5 volumes) was then introduced and the jacket was set to 15° C. 300 mL of deionized $H_2O$ (3 volumes) was charged and the slurry cooled from ~17° C. to 10° C. with stirring at 130 RPM. HCl (86.4 mL, 11.8M, 1.019 mol, 3 equiv.) was added in one portion with the slurry at 10° C. The mixture exothermed to 17.3° C. and the jacket was adjusted to 22° C. The slurry cooled to 13.8° C. before being warmed back up to 20° C. in 13 minutes. The stirring was turned up to 175 RPM to improve mixing while completing a 30 minute age. The solids had dissolved after 30 minutes. At 57 minutes the stirring was stopped and the biphasic solution was allowed to settle and sit overnight (15 h).

After sitting overnight, stirring (175 RPM) was reinitiated and the jacket was set to −40° C. It took 28 minutes for the mixture to reach −15° C. and in that time the jacket was adjusted to −20° C. With the jacket at −20 and the reaction at −15° C. the first charge of N-chlorosuccinimide (NCS) was done (28.4 g, 0.2127 mol, 0.626 equiv.). The reaction exothermed to −1.2° C. in 1.5 minutes. 4 minutes later with the reaction cooled to −6.9° C. and the jacket still at −20° C. the second charge of NCS was done (85.0 g, 0.6367 mol, 1.874 equiv.). The reaction exothermed to 2.2° C. in 1.5 minutes. The reaction was then cooled to 0° C. in 1 minute and held at 0±2° C. Acetonitrile (ACN) (25 mL, 0.25 volumes vs wt % corrected CEP-41609) was used to rinse residual NCS off the wall of the reactor and into the reaction just after the second charge. After 2 hours at 0±2° C. an IPC was taken from the organic layer and the HPLC showed undetectable levels of CEP-41608.

At 2 hours 22 minutes the work up began with the addition of MTBE (650 mL, 6.5 volumes) over 6 minutes at 0 to 1.7° C. The mixture was stirred at 175 RPM (complete mixing achieved) for 2.5 minutes then stirring was stopped and the layers settled in 2.5 minutes. 280 mL of an aqueous layer was then cut at −1.6° C. To the remaining 1500 mL of organic solution was charged 650 mL NaCl solution (6.5 volumes, 24 wt % NaCl; 189.2 g NaCl mixed with 599.25 g D.I. $H_2O$) over 8 minutes at −1.3 to 1.7° C. Stirring was increased to 325 RPM to achieve complete mixing. The solution was allowed to stir for 1.5 minutes before stopping the stirring and allowing the layers settle in 3 minutes. 1000 mL of aqueous layer was cut at −0.4° C. To the remaining 1100 mL of organic layer was charged 650 mL $NaHCO_3$ solution (6.5 volumes, 7.5 wt % $NaHCO_3$; 53 g $NaHCO_3$ mixed with 655.5 g D.I. $H_2O$) over 9 minutes at −0.3 to 2.6° C. with stirring at 325 RPM to achieve complete mixing. The solution was allowed to stir for 5 minutes and then the stirring was stopped and the layers settled in 4 minutes. 800 mL of an aqueous layer (pH=8) was cut at 0.2° C.

The remaining organic layer (1000 mL) was checked by HPLC (70.2 A % CEP-41159, 17.5 A % impurity 1, 5.9 A % impurity 2, 2.9 A % impurity 3). The jacket was set to 10° C. while a solution of $Na_2S_2O_4$ (33.4 g @ 85 wt %, 0.1631 mol, in 326 mL DI $H_2O$) was prepared in a capped Kimax jar. 50 minutes after cutting the $NaHCO_3$ layer the organic layer was at 8.8° C. With the jacket at 10° C. the $Na_2S_2O_4$ solution was added in one portion with the stirring at 250 RPM. The mixture warms to 15.4° C. and the jacket was adjusted to maintain the reaction at 15±1° C. for 15 minutes. Stirring was then stopped and an HPLC was taken from the organic layer while holding the biphasic solution at 15° C. The HPLC showed no detectable impurity 1 (76.1 A % CEP-41159, 6.4 A % impurity 2, 3.1 A % impurity 3, 0.54 A % CEP-41608). After a total of 39 minutes contact time with $Na_2S_2O_4$ solution the aqueous layer was cut leaving 925 mL of organic layer. This solution was held overnight with the jacket at 20° C.

After 16 hours 11 minutes the organic solution was drained into a round bottom flask, rinsing with 100 mL MTBE (1 volume). The solution was then concentrated at 120 mbar with the bath temperature at 35° C. Once 590 mL (5.9 volumes vs. wt % corrected CEP-41609) was removed the remaining solution was diluted with 550 mL AcOH (5.5 volumes vs. wt % corrected CEP-41609). This solution was then concentrated again at 65 mbar with the bath temperature at 45° C. Once 320 mL (3.2 volumes vs. wt % corrected CEP-41609) was removed the distillation was stopped and the remaining solution was weighted (523.39 g) and checked by HPLC and $^1$H NMR. HPLC showed 66.31 g (87.0% yield) of CEP-41159 in solution, and the NMR showed 96.0 wt % AcOH (3.1 wt % ACN, 0.9 wt % MTBE; 93 wt % AcOH desired). The desired AcOH solution mass was calculated from the HPLC assay of CEP-41159 (9×66.31 g=596.79 g) and the amount of AcOH needed to dilute to this mass was also calculated (596.79-523.39=73.4 g×(1 mL/1.049 g)=70 mL AcOH). The AcOH solution was then transferred back to the 2 L JLR (which had been rinsed with $H_2O$ and dried with an $N_2$ sweep and 40° C. jacket) and 70 mL of AcOH was used to rinse out the round bottom flask and dilute the solution.

After sitting at 20° C. for 2.5 hours this solution was diluted with 199 mL DI $H_2O$ (3 volumes vs. CEP-41159) while setting the stirring at 225 RPM and the jacket at −30° C. The resulting homogeneous solution was cooled to −10° C. in 21 minutes. The stirring was set to 324 RPM and after 1 minute at −10° C. seed (249.4 mg, Lot #3292-111-P1) was added to the solution. A thick slurry formed in <2 minutes (exotherms to −8.6° C.) but the stir speed allowed for good mixing. After 29 minutes added 332 mL DI $H_2O$ (5 volumes vs. CEP-41159) over 12 minutes at −10 to −8° C. Held the slurry for 28 minutes at −10° C. and then filtered a sample to check the mother liquor losses. Losses looked good at 7.7 mg/g (desired <9 mg/g). After 50 minutes at −10° C. with all water added the slurry was filtered. Filtration was quick, taking <1 minute. The flask and cake were washed with 265.3 mL of ambient temperature 25 vol % AcOH/$H_2O$ (4 volumes vs. CEP-41159). The resulting mother liquors and wash were assayed and found to contain 6.7% losses (4.0 mg/g CEP-41159). The solids were held on the filter with the vacuum pulling air across them and with aluminum foil keeping light from them.

After 67 hours and the solids were then left on the filter for another 48 hours. A total of 58.08 g of white cottony solids were recovered and were checked by HPLC and ¹H NMR. HPLC indicates the solids were 100 A % and 102.7 wt % while the NMR showed only trace levels of AcOH. Based on this data the solids were deemed 100% pure and the yield was 76.2%.

Example 4

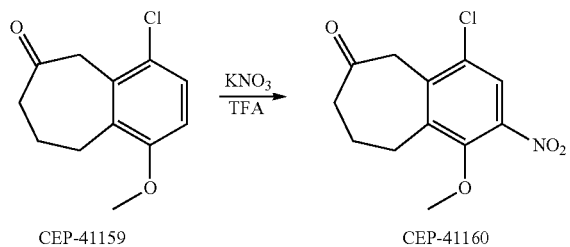

All volumes and equivalents are based on the wt % corrected charge of CEP-41159 unless other wise stated. Potassium nitrate (22.99 g, 0.2274 mol, 1.02 equivalents) was dissolved in trifluoroacetic acid (TFA) (125 mL, 2.5 volumes). This dissolution took ~5 minutes with vigorous stirring. CEP-41159 (50.0 g, 0.2229 mol, 1.00 equivalents) was taken up in TFA (125 mL, 2.5 volumes) at 22° C. This solution was cooled to −13° C. over 21 minutes and then the addition of the potassium nitrate/TFA solution was started. This solution was added in four equal portions. After each portion was added an HPLC was run on a sample of the reaction to evaluate if the reaction had progressed. The sample was diluted in ACN before it could warm up as a temperature rise would likely cause further reaction to occur. The HPLC after the first addition was completed (addition took 13 min at −13 to −6.2° C.) showed 20.9% conversion. The batch was cooled to −13° C. and the second addition was done over 5 minutes at −13 to −1.2° C. HPLC after the second addition showed 43.6% conversion. After the reaction was cooled back to −13° C. the third addition was started. This third addition was done over 5 minutes at −13 to −2.7° C., and the HPLC showed 70.1% conversion. After the reaction was cooled back to −13° C. the final addition was started. This final addition was done over 3 minutes at −13 to −7.5° C., and the HPLC showed 98.9% conversion. The reaction was held at −13° C. while sodium acetate (22.85 g, 0.2787 mol, 1.25 equivalents) was taken up in DI water (600 mL, 12.0 volumes). After 19 minutes at −14 to −13° C. the reaction was diluted with half of the sodium acetate solution over 3 minutes while allowing the reaction to warm from −14° C. to 14.5° C. The resulting solution was warmed to 22° C. over 14 minutes and seeded with CEP-41160 (50 mg, 0.001×CEP-41159). The resulting slurry was allowed to stir overnight. After 15 hours 51 minutes the second half of the sodium acetate solution was added over 12 minutes at 21.6-22.6° C. The resulting slurry was stirred for 34 minutes and then assayed for losses. The losses were at 2.88 mg/g. The slurry was then filtered 1 hour 07 minutes after final sodium acetate solution addition was done. The reaction vessel and cake were washed with DI water (200 mL, 4.0 volumes). The mother liquors and wash were combined and assayed by HPLC to determine they contain 4.3% of the product. The solids were dried in the filter open to air with the vacuum pulling on the bottom of the filter. After 4 hours 52 minutes of drying 52.985 g of CEP-41160 was recovered. These were bright yellow sandy solids which were 100 A % and 100.8 wt % (@ 238 nm). This is 88.3% yield of CEP-41160.

Example 5

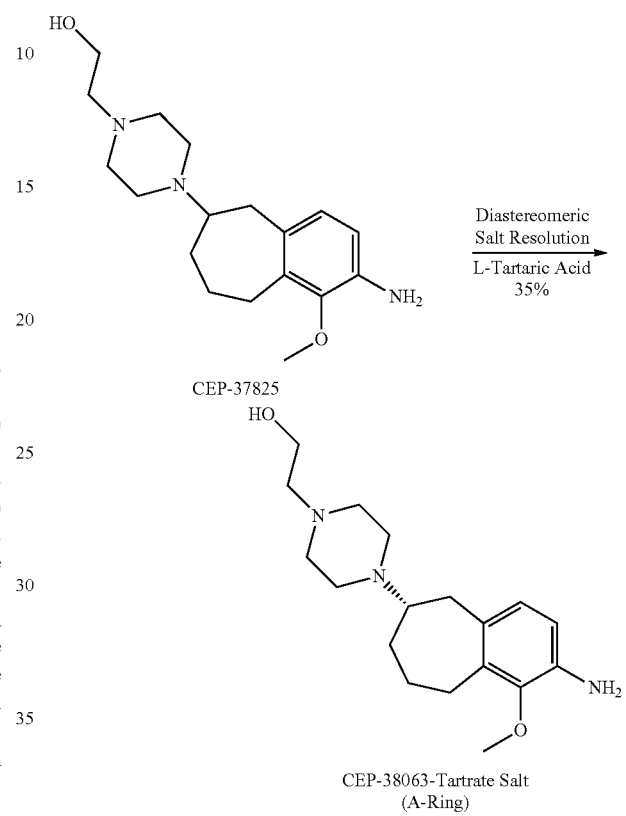

A glass jar was charged with CEP-37825 (17.0 g physical, 16.7 g corrected, 52.3 m mol, 1.00 equiv, Johnson Matthey 4239.A.13.2), MeOH (167 mL) and H₂O (40.5 g). The mixture was stirred at ambient temperature until complete dissolution occurred. The resulting solution was filtered over a sintered glass funnel into a 500 mL jacketed reactor, rinsing with MeOH (85 mL). The reactor was evacuated and filled with N₂. The solution was heated to 35° C. (internal temperature). A solution of L-tartaric acid (7.85 g, 52.3 mmol, 1.00 equiv) in MeOH (84 mL) was added via addition funnel over 11 minutes. Additional MeOH (30 mL) was used as a rinse. The solution was seeded with a slurry of CEP-38063 L-tartrate (50.0 mg) in MeOH (2.5 mL). The vial containing the slurry was rinsed with additional MeOH (1.2 mL). A slurry gradually formed, and the mixture was aged at 33-34° C. for 90 min. The internal temperature was decreased to 29° C. and agitated for 63 min after which the mixture was cooled to 20-25° C. and stirred overnight.

After stirring overnight at ambient temperature, the mixture was filtered, rinsing with a solution of H₂O (2.6 mL) in MeOH (49 mL). The mixture was dried at room temperature overnight under vacuum. Crude CEP-38063 L-tartrate (10.07 g) was obtained in 87.6% de (93.8% dr). The CEP-38063 free base content was 64.2%. The yield was 36% from CEP-37825 racemate.

Recrystallization: A 1 L OptiMax vessel was charged with two lots of crude CEP-38063 L-tartrate (18.9 g, 89.3% dr, 9.47 g, 88.6% de, 57.1 mmol total). Methanol (346 mL) and H$_2$O (38.8 g) were added and the reactor was placed under nitrogen. The slurry was heated to 66.5° C. during which time the solids dissolved. The solution was then cooled to 55° C. and seeded with a slurry of CEP-38063 L-tartrate (106.9 mg) in MeOH (5.4 mL). The vial containing the slurry was rinsed with additional MeOH (2.6 mL). The slurry was agitated at 53-54° C. for 82 min. It was then cooled to 48.5° C. over 60 minutes. It was agitated for 1 h, then cooled to 20° C. over 60 minutes.

After stirring overnight at ambient temperature, the mixture was filtered, rinsing with a solution of H$_2$O (5.7 mL) in MeOH (107 mL). The mixture was dried under vacuum at room temperature overnight. CEP-38063 L-tartrate (21.4 g) was obtained in >99 A %, 99.4% de (99.7% dr). The CEP-38063 free base content was 65.3%.

Other resolution studies were conducted. See Tables 1-4.

TABLE 1

L-Tartaric Acid Salt Screen Results

| Entry | Solvent (% v/v H$_2$O) | Scale (mg) | Wet cake (% de) | Filtrate loss of desired enantiomer |
|---|---|---|---|---|
| 1 | MeOH (anh) | 100 | 22.3 | 14% |
| 2 | MeOH (1%) | 80 | 35.3 | 14% |
| 3 | MeOH (5%) | 80 | 76.8 | 20% |
| 4 | MeOH (5%) | 310 | 83.8 | 20% |

A 96-member salt screen was completed concurrently, using racemic CEP-37825 (1.0 g) with the Chirosolv Acid Series 1 resolving kit. 8 acids and 12 solvent systems were employed in this kit with a 1:1 ratio of free base to acid. After heating salts at 80° C. and cooling, the supernatants of those vials containing solids were examined for both diastereomeric excess (with respect to the undesired CEP-38062 salt) as well as the concentration of CEP-38062 remaining in solution. See Table 2.

TABLE 2

| Entry | Solvent | Acid | Supernatant purity (% de) | CEP-38062 supernatant conc. (mg/mL) |
|---|---|---|---|---|
| 1 | EtOH | (−)-CSA | 3.5 | 18.5 |
| 2 | EtOH | (−)-CSA | 1.8 | 16.7 |
| 3 | EtOH | (+)-tartaric | 17.4 | 2.5 |
| 4 | MeOH | (+)-tartaric | −2.4 | 11.8 |
| 5 | 2-PrOH | (+)-tartaric | −0.2 | 12.5 |
| 6 | i-BuOH | (+)-tartaric | −0.4 | 20.7 |
| 7 | 1-PrOH | (+)-tartaric | −0.8 | 17.0 |
| 8 | EtOH | (−)-DTTA | 45.5 | 35.6 |
| 9 | EtOH (95%) | (−)-DTTA | 10.5 | 16.0 |
| 10 | MeOH | (−)-DTTA | 18.7 | 21.2 |
| 11 | 2-PrOH | (−)-DTTA | 51.1 | 8.8 |
| 12 | 2-PrOH (90%) | (−)-DTTA | 37.9 | 12.7 |
| 13 | i-BuOH | (−)-DTTA | 45.9 | 7.1 |
| 14 | H$_2$O | (−)-DTTA | 0 | 3.1 |
| 15 | (CH$_2$OH)$_2$ (75%) | (−)-DTTA | 7.7 | 11.4 |
| 16 | 1-PrOH | (−)-DTTA | 48.7 | 14.6 |

The conditions from entries 8, 10, 11, and 16 (Table 2) were repeated on a 80 mg scale in a round-bottom flask. The racemic freebase was dissolved in solvent at elevated temperature (50-60° C.), and (−)-DTTA (1.0 equiv) was added as a solution. In each case, solids formed immediately. The mixtures were cooled to room temperature, stirred overnight, and filtered. Wet cake solids, and supernatants were analyzed. In each case the supernatant concentrations of the undesired diastereomeric salt were much lower than they were in the initial screen. See Table 3.

TABLE 3

| Entry | Solvent | Wet cake purity (% de) | Supernatant purity (% de) | CEP-38062 supernatant conc. (mg/mL) |
|---|---|---|---|---|
| 1 | MeOH | 13.8 | 64.7 | 6.2 |
| 2 | EtOH | 2.7 | 60.1 | 1.1 |
| 3 | 1-PrOH | 1.7 | 52.6 | 0.7 |
| 4 | 2-PrOH | 0.9 | 46.7 | 0.4 |

A second 96-member salt screen was completed using racemic CEP-37825 (1.0 g) with the Chirosolv Acid Series 2 resolving kit. 8 acids and 12 solvent systems were employed in this kit with a 1:1 ratio of free base to acid. This screen resulted in more oils than the first screen. See Table 4.

TABLE 4

| Entry | Solvent | Acid | Supernatant purity (% de) | CEP-38062 supernatant conc. (mg/mL) |
|---|---|---|---|---|
| 1 | H$_2$O | (+)-DCA | −44.2 | 4.0 |
| 2 | 1-BuOH | Z(−)-quinic | −0.36 | 8.4 |
| 3 | 2-PrOH | (−)-quinic | −1.1 | 14.4 |
| 4 | 2-PrOH (90%) | (−)-quinic | −1.2 | 12.8 |
| 5 | i-BuOH | (−)-quinic | −1.8 | 11.1 |
| 6 | 1-PrOH | (−)-quinic | −1.4 | 14.7 |
| 7 | EtOH | (−)-DBTA | 25.2 | 8.1 |
| 8 | EtOH (95%) | (−)-DBTA | 9.6 | 11.6 |
| 9 | 2-PrOH | (−)-DBTA | 33.2 | 11.7 |
| 10 | 2-PrOH (90%) | (−)-DBTA | 16.1 | 14.8 |
| 11 | i-BuOH | (−)-DBTA | 6.2 | 4.7 |
| 12 | H$_2$O | (−)-DBTA | 7.74 | 4.9 |
| 13 | 1-PrOH | (−)-DBTA | 9.4 | 13.1 |
| 14 | EtOH | (−)-tartaric | 0.81 | 6.6 |
| 15 | EtOH (95%) | (−)-tartaric | 0.27 | 4.7 |
| 16 | 2-PrOH | (−)-tartaric | −.62 | 4.7 |
| 17 | i-BuOH | (−)-tartaric | 0.63 | 8.6 |
| 18 | 1-PrOH | (−)-tartaric | −1.9 | 9.0 |

Example 6: Procedure for CEP-19036 (Amidation and Coupling Step)

Into a 20-L jacketed glass reactor were charged isatoic anhydride (500 g, 3.06 mol,) and ethanol (2500 mL). This was followed by the controlled addition of 30 wt % methylamine in ethanol (378.5 g, 3.98 mol) further diluted with ethanol (330 mL) over 70 minutes from an addition funnel at 20±5° C. The resulting mixture was stirred at 20±5° C. for 60 min and checked by HPLC for reaction completion (<1 A % SM). Upon completion, 13% NaCl (prepared by dissolving 390 g of NaCl in 2610 mL of DI water) was added over 20.0 min. The resulting mixture was agitated at 20±5° C. for 10 min then allowed to settle for 10 min. The bottom aqueous layer was removed. The organic layer was washed with 26% NaCl (prepared by dissolving 792 g of NaCl in 2210 mL of DI water). The combined aqueous washes were extracted with ethyl acetate (5100 mL). The ethyl acetate extract was combined with the batch and concentrated under reduced pressure (50-80 mmHg) at 30-40° C. in a 12-L round-bottomed flask until the batch volume was approximately 1.5 L (3×the weight of isatoic anhydride). To the residue was added ethyl acetate (5100 mL), which was then concentrated under reduced pressure (50-80 mmHg), a second time, to approximately 1.5 L (3×the weight of isatoic anhydride). To the concentrated batch was added 5.0 L of acetonitrile. The resulting mixture was stirred at room temperature for 60 min, and filtered through a pad of Celite in a sintered glass funnel with fine porosity. The pad was rinsed with acetonitrile (500 mL) and the rinse was combined with the batch. The clear filtrate was transferred to a 20-L jacketed glass reactor. Hunig's base (712.6 g) and 2,4,5-trichloropyrimidine (657.3 g) were added. The resulting solution was heated to 73±3° C. and agitated at 73±3° C. until the reaction was complete as indicated by an in-process test. The reaction mixture was then cooled to 0±5° C. over 30 min and stirred at this temperature for 1-2 hrs. The product was collected by vacuum filtration on a sintered glass funnel. The cake was rinsed with acetonitrile (1240 mL) and pulled dry under vacuum with a nitrogen bleed until the residual water and acetonitrile content were less than 1 wt % by NMR analysis and KF titration. A total of 746.3 g (81.9% overall yield) of CEP-19036 was obtained as a light tan solid with the following quality attributes: 99.8 A %, 98.99 wt %, 0.1 wt % NaCl, 0.1 wt % $H_2O$, 0.1 wt % acetonitrile.

Example 7

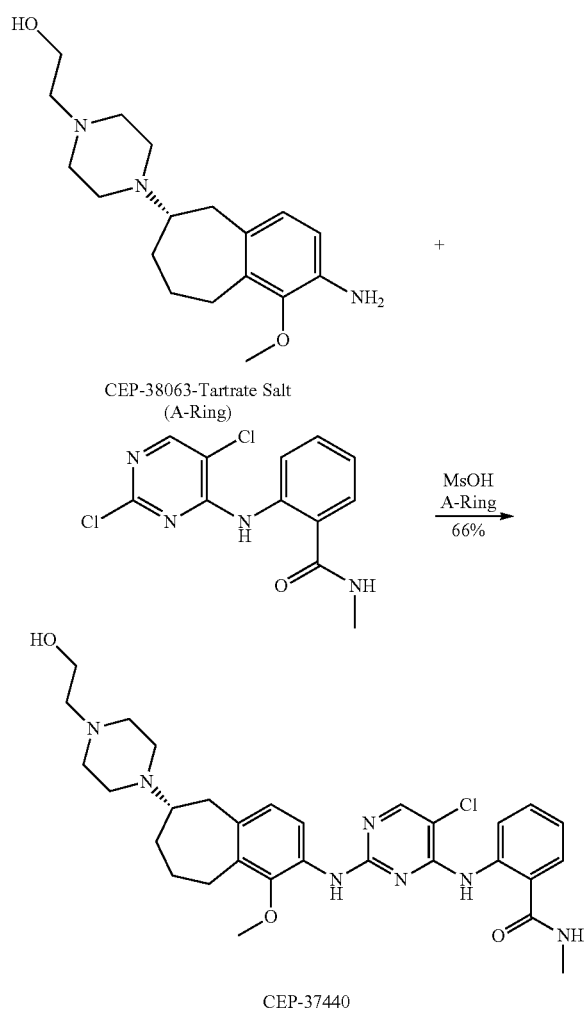

CEP-38063-tartrate salt (30.1 g of salt, Limiting Reagent) was charged to a vessel along with 10 volumes of water and 10 volumes of dichloromethane. At room temperature NaOH (10 N aqueous solution, 2 equiv) was added and stirred for 15 minutes. The bottom organic layer was removed and the aqueous layer was washed a second time with 10 volumes of dichloromethane. The combined organics were washed with brine (5 volumes) then concentrated under vacuum by distillation. To the concentrate, 1-methoxy-2-propanol (12.7 volumes) was added along with CEP-19036 (1.25 equiv) and methanesulfonic acid (2.75 eq). The resulting mixture was heated to 70° C. for approximately 48 hours then cooled to room temperature. Water (14 volumes) and dichloromethane (14 volumes) was added and stirred for 15 minutes. The bottom organic layer was cut to waste prior to adding an additional 14 volumes of dichloromethane and NaOH (10N, 3.6 equiv). The bottom organic layer was removed and the aqueous was washed with an additional 14 volumes of dichloromethane. The organic layers were combined, washed with brine and concentrated under vacuum by distillation. Isopropanol (30 volumes) and water (0.6 volumes) was added and heated to 70° C. The resulting solution was cooled to 50° C. before adding additional water (5.8 volumes) which results in crystallization. The slurry was then cooled to room temperature, filtered and dried at 60° C. to afford a 74% yield of product with >99% purity.

Example 8: Procedure for CEP-37440-$_3$HCl-2H$_2$O (Salt Formation)

Combined free base (145.83 g, 251.4 mmol) into a 5 L 3-neck round bottom flask equipped with overhead stirring and an addition funnel. To these solids was added nBuOH which resulted in a yellow cloudy solution (free of large solids) after stirring for 40 minutes. Precipitation occurred immediately and a slight exotherm to 23° C. was observed. The resulting slurry was heated to 85° C. over 45 minutes. Near 60° C., the solids went into solution. Once the heating reached 80° C., HCl (2.5 M in 1:1:1 MeOH/EtOH/water, 307 mL, 767 mmol) was added via addition over 4 minutes and seed crystals (CEP-37440 H2A3, 1.7 g) were added. The seed held and more solids formed during a 1 h age at 85° C. The solution was then cooled to room temperature over 1 h then further cooled to 2° C. over an additional 30 minutes. The slurry was stirred at 0-5° C. for 1 h then filtered, washing with 0° C. nBuOH (400 mL). Initial cake dimensions (cylinder) were 6.0 cm high with a diameter of 13.5 cm. After wash, compressed cake was 4.3 cm high. Losses to the mother liquor were approximately 0.5%. The resulting solids were dried in a vacuum oven at 60° C. for 24 h (with N$_2$ purging after the first 16 h) to give 162 g of the desired product (98.8 HPLC purity, 88% isolated yield assuming 100 wt % starting material, 0.5% residual nBuOH by NMR, XRPD and m.p. confirmed H2A3 salt form).

Example 9: Enamine Formation and Hydrogenation

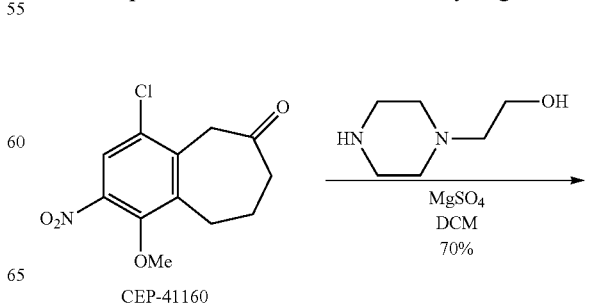

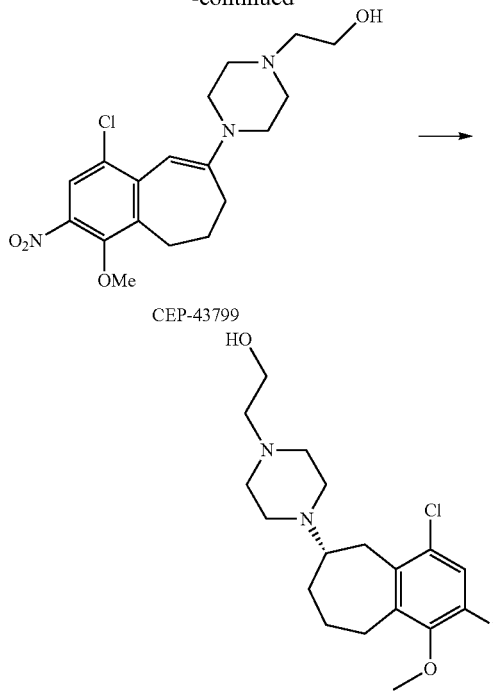

CEP-43799

To CEP-41160 (10 g) was added MgSO$_4$ (2.5 g, 25 wt %) and dichloromethane (8 volumes wrt CEP-41160) at room temperature and stirred for 4 days. The resulting slurry was filtered and the filtrant was concentrated to an oil. The oil was then taken up into MTBE (70 mL, 7 volumes) which resulted in crystallization. The slurry was cooled to 0° C. and the product was filtered washing with cold MTBE. The product was dried with nitrogen under vacuum to afford 10.5 g of the product (68%). Additional MTBE crystallizations could be applied to increase purity as desired.

Prior to the reaction, the NaBArF was dried by co-evaporation with dry toluene (3 times) to remove traces of water. Trifluoroethanol was dried over molecular sieves (Union Carbide, Type 13X). In a pre-dried Schlenk, the appropriate amount of [Ir(COE)$_2$Cl]$_2$ precursor and RD81 was dissolved in dry DCM. After stirring the solution for 30 minutes, the NaBArF was added and stirred for an additional 30 minutes. In a separate Schlenk, the appropriate amount of substrate was dissolved in dry trifluoroethanol and stirred for 30 minutes. To a pre-dried high-pressure autoclave both the catalyst solution and substrate solution were transferred under a gentle stream of dry nitrogen. The autoclave was closed and pressurized to 50 bars of hydrogen and stirred for the desired reaction time. Then, the autoclave was vented and the reaction mixture collected. Work-up of the samples: all volatiles were removed in vacuo.

The production of 40 grams of product was performed according to the following Table 5.

TABLE 5

|  | Run 1 (0.2M) | Run 2 (0.3M) |
| --- | --- | --- |
| [IR(COE)$_2$Cl$_2$]$_2$ (Strem, Lot 20534600) | 1.0 mM | 1.0 mM |
| NaBArF | 1.2 equiv. | 1.2 equiv. |
| Ligand RD81 (Lot ZA395) | 4.4 equiv. | 4.4 equiv. |
| Temperature | 21° C. | 21° C. |
| Pressure H$_2$ (Praxair, 5.0) | 50 bar | 50 bar |
| Time | 20 h | 20 h |

TABLE 5-continued

|  | Run 1 (0.2M) | Run 2 (0.3M) |
| --- | --- | --- |
| Solvent | DCM/TFE | DCM/TFE |
| TFE (ABCR, Lot 1031206) | 66% | 66% |
| Substrate (CEP-43799) (Lot: 43487-72) | 0.2M | 0.3M |
| Total volume | 450 mL | 360 mL |
| Stirring speed | 1000 rpm | 1750 rpm |
| System | 1L autoclave | 1L autoclave |

Example 10

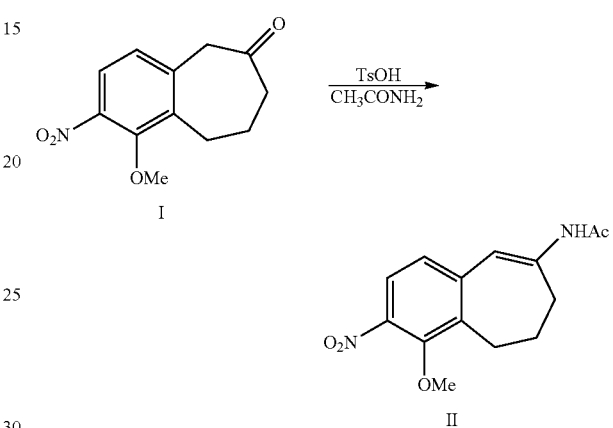

Preparation of hydrogenation substrate was accomplished by condensation of the ketone (1 eq.) and amide (1.1 eq.-1.3 eq) catalyzed by TsOH (0.05 eq. to 0.1 eq.) in toluene.

To a solution of I (4.7 g, 20 mmol) in toluene (30 mL, 7 vol) was added acetamide (1.54 g, 26 mmol, 1.3 equiv) and TsOH.H$_2$O (0.02 g, 1 mmol, 0.05 equiv.). The mixture was refluxed under N$_2$ equipped with a Dean-Stark apparatus to remove H$_2$O. The progress of the reaction was monitored by TLC. When the reaction was completed, the mixture was cooled down. The solution was washed with H$_2$O, dried over Na$_2$SO$_4$ and concentrated. The residue was purified by silica gel column chromatography with hexane/ethyl acetate (5/1→1/1, v/v) as eluent to give the desired product as a yellow solid (5.0 g, 90% yield).

Example 11

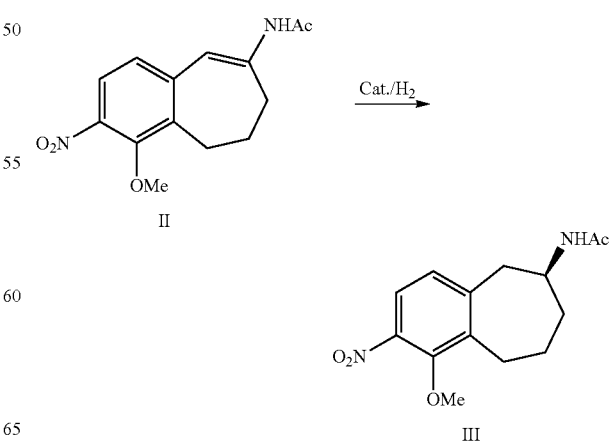

Asymmetric hydrogenations were conducted using catalytic Ru(R—C$_3$-TunePhos)(acac)$_2$ in methanol with 0.25 eq. of H$_3$PO$_4$ (20 mg/mL), at about 30, 50, and 70° C. using 10, 20, 35, 50, and 70 atm of H$_2$. Reaction times were about 15-18 h. Conversions of >99% were achieved. Enantiomeric excesses (%) of 67%-82% were observed.

Example 12

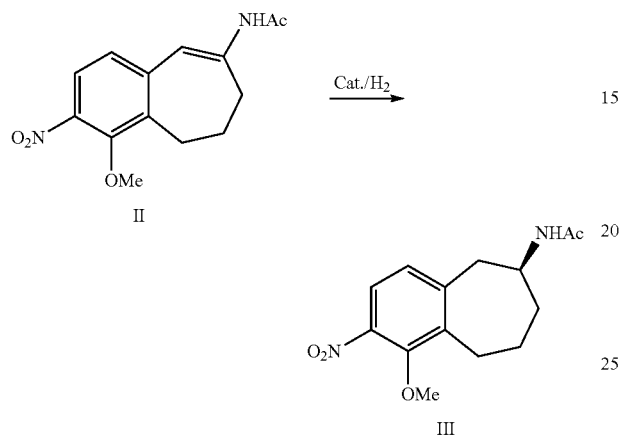

Asymmetric hydrogenations were conducted using catalytic Ru(S—O$_5$-TunePhos)(acac)$_2$ in methanol or ethanol with 0.063 eq., 0.125 eq. 0.25 eq., and 0.5 eq. of H$_3$PO$_4$ (20 mg/mL), at about 50, 70, and 90° C. using 20, 50, 70, and 75 atm of H$_2$. Reaction times were about 15-18 h. Conversions of >99% were achieved. Enantiomeric excesses (%) of 79%-86% were observed.

Example 13

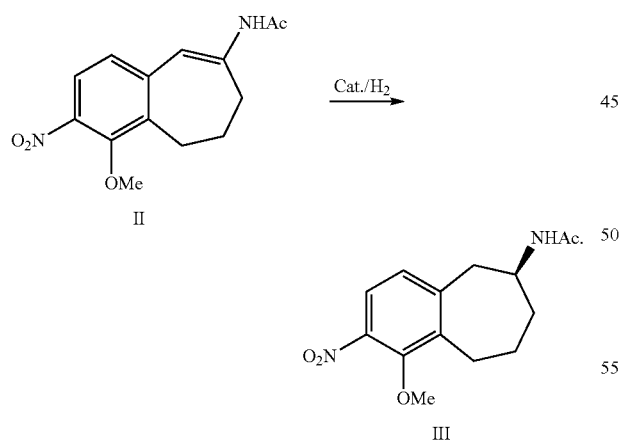

In a glove box, to a hydrogenator (with glass liner) were added the substrate (4.14 g, 15 mmol), Ru(S—C$_5$-TunePhos)(acac)$_2$ (13.8 mg, 0.015 mmol, TON1000), H$_3$PO$_4$ (9 mL, 20 mg/mL in CH$_3$OH, 0.125 equiv), CH$_3$OH (19 mL, 7 vol) and a magnetic stirring bar. The hydrogenator was sealed and taken out of the glove box. The hydrogenator was charged with hydrogen to 50 atm. and put in an oil bath. The reaction mixture was stirred under 50 atm. at 50° C. for 48 h. After hydrogen was released carefully, the reaction mixture was concentrated. Recrystallization from CH$_3$OH (55 mL) gave the desired product as an off-white solid (2.29 g, 55% yield).

REFERENCES

Allwein, S. P et al., Org. Process Res. Dev. 2012, 16, 148-155.
Purohit, V. C. Org. Lett. 2013, 15, 1650-1653.
WO2008/051547

What is claimed:
1. A method comprising
resolving a mixture of compounds IA and IB

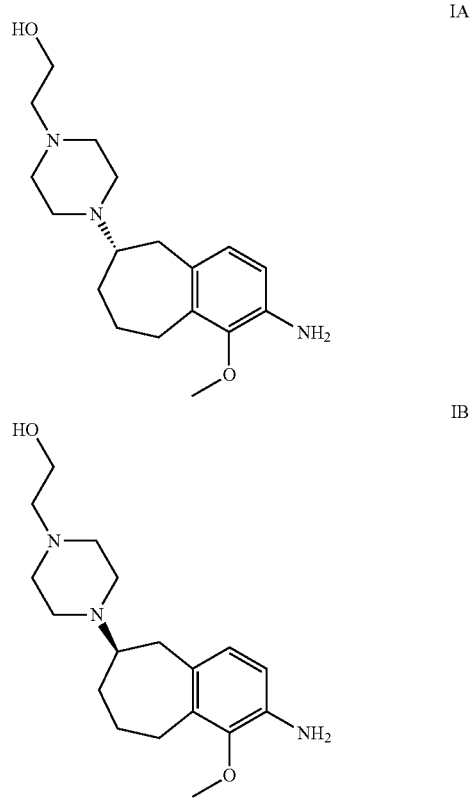

in the presence of L-tartaric acid;
in a solvent system comprising an alcohol and water;
to produce the L-tartaric acid salt of the compound IA.
2. The method of claim 1, wherein the alcohol is methanol.
3. The method of claim 1, wherein the L-tartaric acid salt of the compound IA is produced with a diastereometric excess of at least 85%.
4. The method of claim 1, wherein the resolving is carried out at a temperature of between about 15 to about 40° C.
5. The method of claim 1, wherein the concentration of the mixture of compounds IA and IB in the solvent system is about 0.02 g/mL to about 1 g/mL.
6. A method comprising
contacting a compound of formula IV, or a salt form thereof

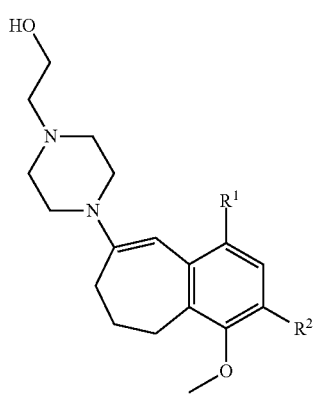

IV wherein R¹ is H, Cl, Br, or I; and R² is NO₂ or NH₂;
with a first hydrogenation catalyst, a ligand, and optionally an additive, in the presence of hydrogen to form a compound of formula V, or a salt form thereof

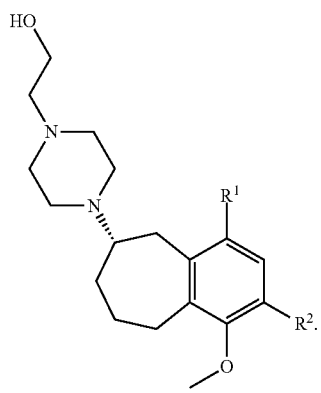

V

7. The method of claim 6, wherein the first hydrogenation catalyst is an iridium catalyst, a rhodium catalyst, or a ruthenium catalyst.

8. The method of claim 7, wherein the first hydrogenation catalyst is bis((μ-chloro)bis(cyclooctene)iridium.

9. The method of claim 6, wherein the ligand is METAMORPhos.

10. The method of claim 6, wherein the additive is a borate.

11. The method of claim 10, wherein the borate is sodium tetrakis[3,5-bis(trifluoromethyl)phenyl]borate.

12. The method of claim 6, wherein the hydrogen is at a pressure of greater than atmospheric pressure.

13. The method of claim 6, wherein the method is performed in the presence of an organic solvent.

14. The method of claim 13, wherein the organic solvent is trifluoroethanol, dichloromethane, or a mixture thereof.

15. The method of claim 6, further comprising contacting the compound of formula V with hydrogen and a second hydrogenation catalyst for a time sufficient to produce the compound IA, or a salt thereof

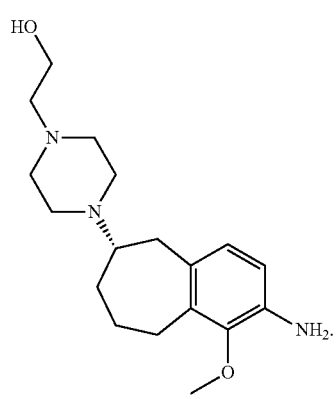

IA

16. The method of claim 15, wherein the second hydrogenation catalyst is palladium.

17. The method of claim 15, wherein the pressure of the hydrogen is about 1 atm or between about 1 atm and 8 atm.

18. The method of claim 15, further comprising converting the compound IA to a salt of the compound IA.

19. The method of claim 18, wherein the salt is the tartrate salt of the compound IA.

20. The method of claim 6, wherein the compound of formula IV is produced by a process comprising contacting a compound of formula II

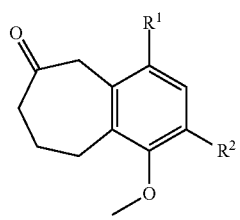

II with a compound of formula III, or a salt form thereof

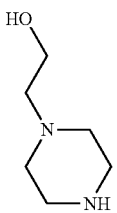

III for a time and under conditions sufficient to produce the compound of formula IV, or a salt form thereof.

21. The method of claim 20, wherein the compound of formula II is produced by a process comprising contacting a compound of formula IIA, or a salt form thereof

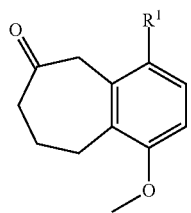

IIA with a nitrate in the presence of an acid to form the compound of formula II wherein $R^2$ is $NO_2$; and optionally reducing the $NO_2$ moiety to form the compound of formula II wherein $R^2$ is $NH_2$.

22. The method of claim 21, wherein the nitrate is potassium nitrate or sodium nitrate.

23. The method of claim 21, wherein the acid is trifluoroacetic acid, methanesulfonic acid, or sulfuric acid.

24. A method comprising contacting a compound of formula VI, or a salt form thereof

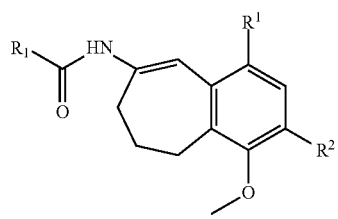

VI wherein $R_1$ is $C_{1-6}$alkyl; and $R^2$ is $NO_2$ or $NH_2$, with hydrogen, a chiral hydrogenation catalyst, and an acid;

in the presence of an organic solvent;

for a time and at a temperature sufficient to produce a compound of formula VII, or a salt form thereof

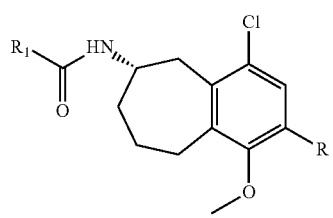

VII wherein R is —$NO_2$ or —$NH_2$.

25. The method of claim 24, wherein the compound of formula VII

26. The method of claim 24, wherein the compound of formula VII is

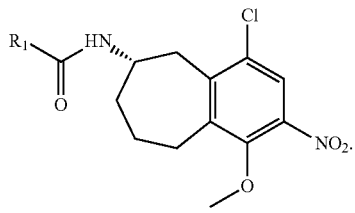

VII-A

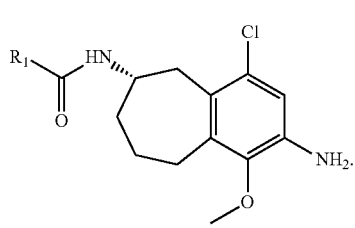

VII-B

27. The method of claim 24, wherein the chiral hydrogenation catalyst is Ru(R—$C_3$-TunePhos)(acac)$_2$, Ru(R—$C_3$-TunePhos)(OAc)$_2$, Rh(COD)(SCRP-DuanPhos)BF$_4$, or Ru(S—$C_5$-TunePhos)(acac)$_2$.

28. The method of claim 24, wherein the organic solvent is an alcohol, toluene, or a combination thereof.

29. The method of claim 24, wherein the acid is a mineral acid.

30. The method of claim 24, wherein the pressure of the hydrogen is between about 10 and about 100 atm or between about 15 and about 70 atm.

31. The method of claim 24, wherein the contacting is conducted at a temperature of about room temperature to about 80° C.

32. The method of claim 24, wherein the enantiomeric excess of the compound of formula II is at least 75%.

33. The method of claim 24, further comprising contacting the compound of formula VII with (2,6-dioxo-morpholin-4-yl)-acetic acid, for a time and under conditions sufficient to produce a compound of formula VIII, or a salt form thereof

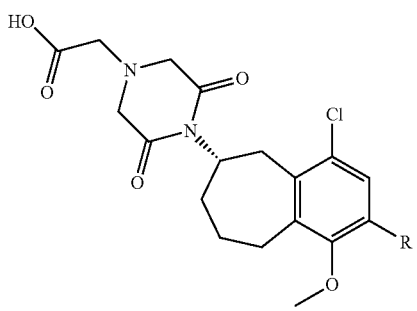

VIII wherein R is —$NO_2$ or —$NH_2$.

34. The method of claim 33, wherein the compound of formula VIII is

VIII-A
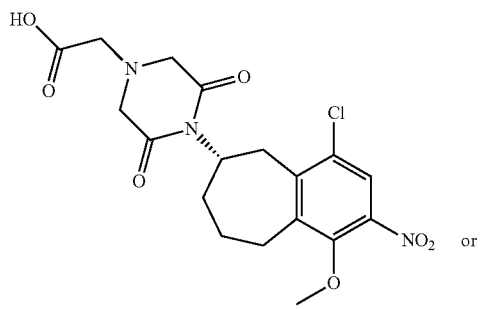
or
VIII-B
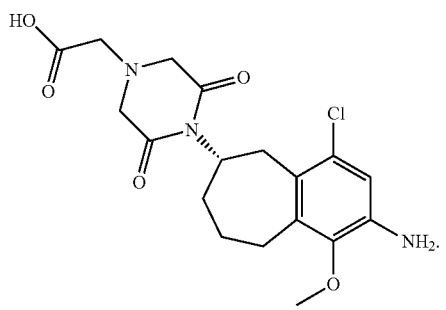
35. The method of claim 33, further comprising subjecting the compound of formula VIII to reducing conditions to form a compound IA, or a salt form thereof
IA
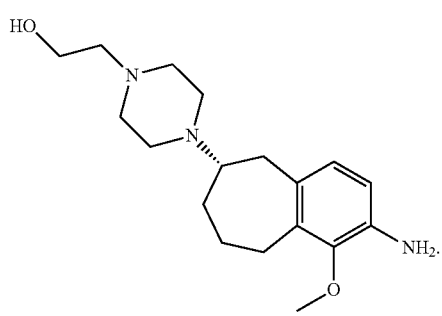
36. A method comprising contacting a compound of formula IX
IX
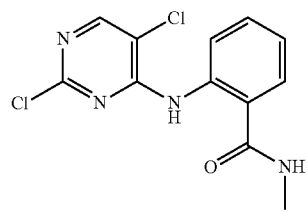
with a compound IA, or a salt form thereof
IA
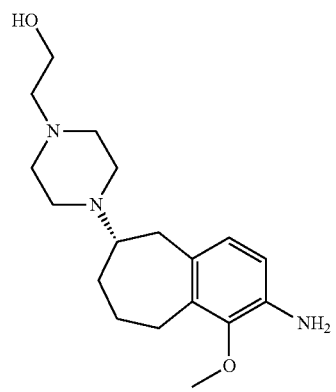
produced according to claim 15, to produce a compound that is CEP-37440, or a salt form thereof
CEP-37440
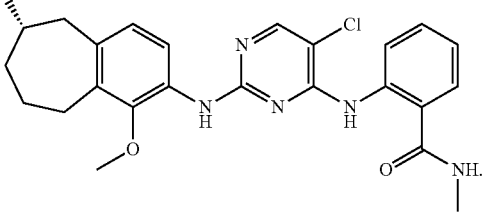
* * * * *